(12) United States Patent
Devi et al.

(10) Patent No.: US 9,415,442 B2
(45) Date of Patent: Aug. 16, 2016

(54) STABLE OXIDE ENCAPSULATED METAL CLUSTERS AND NANOPARTICLES

(75) Inventors: Nandini R. Devi, Maharashtra (IN); Anupam Samanta, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 133 days.

(21) Appl. No.: 14/110,804

(22) PCT Filed: Apr. 11, 2012

(86) PCT No.: PCT/IN2012/000260
§ 371 (c)(1),
(2), (4) Date: Jan. 28, 2014

(87) PCT Pub. No.: WO2012/140675
PCT Pub. Date: Oct. 18, 2012

(65) Prior Publication Data
US 2014/0221199 A1    Aug. 7, 2014

(30) Foreign Application Priority Data

Apr. 11, 2011  (IN) .......................... 1034/DEL/2011

(51) Int. Cl.
| | |
|---|---|
| *B22F 1/02* | (2006.01) |
| *B22F 9/24* | (2006.01) |
| *B22F 1/00* | (2006.01) |
| *B82Y 30/00* | (2011.01) |
| *C22C 5/02* | (2006.01) |
| *C22C 5/04* | (2006.01) |
| *C22C 5/06* | (2006.01) |
| *B01J 23/42* | (2006.01) |
| *B01J 23/44* | (2006.01) |
| *B01J 23/52* | (2006.01) |
| *C09K 11/02* | (2006.01) |
| *G01N 33/58* | (2006.01) |
| *B82Y 5/00* | (2011.01) |

(52) U.S. Cl.
CPC . *B22F 1/02* (2013.01); *B01J 23/42* (2013.01); *B01J 23/44* (2013.01); *B01J 23/52* (2013.01); *B22F 1/0018* (2013.01); *B22F 9/24* (2013.01); *B82Y 30/00* (2013.01); *C09K 11/025* (2013.01); *C22C 5/02* (2013.01); *C22C 5/04* (2013.01); *C22C 5/06* (2013.01); *G01N 33/587* (2013.01); *B82Y 5/00* (2013.01); *Y10S 977/81* (2013.01); *Y10S 977/89* (2013.01); *Y10S 977/92* (2013.01)

(58) Field of Classification Search
None
See application file for complete search history.

(56) References Cited

U.S. PATENT DOCUMENTS

| | | | | |
|---|---|---|---|---|
| 6,586,785 | B2 * | 7/2003 | Flagan .................. | B82Y 10/00 257/261 |
| 7,361,410 | B2 * | 4/2008 | Zhang .................. | G01N 21/658 427/216 |
| 9,051,583 | B2 * | 6/2015 | Mirkin ................... | C12N 15/87 |

OTHER PUBLICATIONS

Cliffel, David E. et al., "Mercaptoammonium-Monolayer-Protected, Water-Soluble Gold, Silver, and Palladium Clusters", Langmuir, vol. 16, pp. 9699-9702, Published on Web Nov. 10, 2000.*
Garcia-Martinez J. et al; "Incorporation of Pd nanoparticles in mesostructured silica"; Microporous and Mesoporous Materials, Elsevier Science Publishing, New York, vol. 117, No. 1-2, p. 170-177, 2009.
Minkee Choi et al; "Mercaptosilane-Assisted Synthesis of Metal Clusters within Zeolites and Catalytic Consequences of Encapsulation", Journal of the American Chemical Society, vol. 132, No. 26, p. 9129-9137, 2010.
Si-Han Wu et al.; "Catalytic nano-rattle of Au@hollow silica: towards a poison-resistant nanocatalyst"; Journal of Materials Chemistry; vol. 21, No. 3, p. 789; 2001.
Zoltan Konya et al.; "Synthetic Insertion of Gold Nanoparticles into Mesoporous Silica"; Chemistry of Materials; vol. 15, No. 6, pp. 1242-1248; 2003.
Anupam Samanta et al.; "Ultrasmall Gold Cluster Arrays Encapsulated in Silica Nanospheres: Applications in Fluorescence Imaging and Catalysis"; Journal of Physical Chemistry C; vol. 116, No. 2, pp. 1748-1754, 2012.
International Search Report dated Jul. 16, 2012 for International Application No. PCT/IN2012/000260.

* cited by examiner

*Primary Examiner* — George Wyszomierski
(74) *Attorney, Agent, or Firm* — Abelman, Frayne & Schwab (57) ABSTRACT

The present invention discloses stable, non-agglomerated, ultra-small metal/alloy clusters encapsulated in silica with the metal/alloy cluster size of less than 5 nm. The invention further discloses a simple, cost effective process for the preparation of metal/alloy clusters encapsulated in silica which is thermally stable and without agglomeration.

2 Claims, 9 Drawing Sheets

STABLE OXIDE ENCAPSULATED METAL CLUSTERS AND NANOPARTICLES

TECHNICAL FIELD OF INVENTION

The present invention relates to stable, non-agglomerated ultra-small metal/alloy clusters encapsulated in silica with the metal/alloy cluster size of less than 5 nm. The metal clusters have unique optical properties and show utilization in bio-imaging applications. The invention further relates to a simple, cost effective process for the preparation of metal/alloy clusters encapsulated in silica which is thermally stable and without agglomeration.

BACKGROUND AND PRIOR ART

Ultra small metal clusters of sizes ranging from sub nanometer to ~2 nm are unique in the manifestation of their optical, magnetic and electronic properties when compared to nanoparticles of bigger sizes. Improved methods of synthesis, purification and characterization of such metal clusters are the subject matter of various research projects and publications.

However, currently widespread exploitation of these materials is fraught with limitations due to the difficulty in manipulation of cluster colloidal solutions with their inherent instability, chemical reactivity and tendency for agglomeration. Hence, more stable water dispersible clusters and the ability to modify and functionalize them are highly desirable for their potential use in various applications.

Coating with inert oxides like silica has been developed in the recent past as a means to enhance surface interactions, biocompatibility and stability in case of bigger faceted nanoparticles. Various classical methods like Stober method, use of silane coupling agents and recently, microemulsion methods are employed to achieve core shell architectures of type Au@SiO2 in such cases.

A review article titled "Quantum sized, thiolate-protected gold nanoclusters" by Rongchao Jin et. al in Nanoscale, 2010, 2, 343-362 summarizes various advances made in the synthesis of achieving ultra-small gold nanoparticles. The review article focuses primarily on a special type of ultra-small gold nanoparticles (<2 nm core diameter) protected by thiolate ligands. The review article further disclose the use of strong ligands such as thiols to stabilize the clusters with a thiol:Au ratio of 3:1. It further states the functionalization of nano clusters with ligands to prevent aggregation/agglomeration.

A review article 'Recent Progress on Silica Coating of Nanoparticles and Related Nanomaterials' by Andre's Guerrero-Martinez et. al in Adv. Mater. 2010, 22, 1182-1195 review the processes for silica coating of colloidal nanoparticles. Various wet chemical approaches are discussed for the synthesis of both spherical and anisometric nanoparticles and nanocomposites, using polymers and surfactants as the "shape-inducing" agent. The article further disclose these of CTAB for preparation of periodic, mesoporous organosilica hollow spheres with tunable wall thickness and states that surface modification with stabilizers greatly assists the transfer of nanoparticles from water into various solvents (such as ethanol), where silica coating can be achieved through controlled hydrolysis and condensation of TEOS.

However, the processes described in the art has not been successfully transferred to encapsulating gold clusters in silica. This may be due to inherent problems of stability of clusters under coating conditions usually employed. Hence the prospect of synthesizing stable clusters under reaction conditions and encapsulating them in a sufficiently space separated manner has been an area unaddressed in the art.

In utilizing noble metal nanoparticles (NPs) for catalysis, the most adverse effect occurs via loss of activity due to agglomeration and subsequent variations in surface properties. Moreover, presence of surface functionalization restricts the widespread use of such materials in catalysis under harsh conditions. To exploit the excellent properties of nanoparticles for a wide range of reaction conditions, it is imperative to protect them from agglomeration at the same time keeping the surface properties intact and surface sites accessible to reactant molecules. This is to an extent achieved in supported catalysts but the propensity of noble metals for sintering as well as leaching of active metal sites plague these systems also. However, recently nanoparticles encapsulated in porous oxides have attracted attention for their potential to address these issues. Even though coating of nanoparticles with oxides, especially silica is a well advanced field of research, frequently used to stabilise the nanoparticles, such a material will not be conducive for catalytic processes. The main drawback is a complete encapsulation of the nanoparticles (NPs) by dense oxide layers denying reactant molecules access to the active surface sites. Thus a simple method using the silica encapsulated clusters as precursors are explored.

OBJECTIVE OF THE INVENTION

The main object of the invention to provide a stable, non-agglomerated ultra small metal/alloy clusters encapsulated in the inert oxide such as silica. The ultra-small metal/alloy clusters of the invention is stabilized in water, has less than 100 atoms and the cluster size less than 5 nm. The ultra-small metal/alloy clusters of the invention can be used as catalyst, display unique optical properties and show utilization in bio-imaging applications.

The other object of the invention is to provide a facile process for the synthesis of non-agglomerated ultra small metal/alloy clusters encapsulated in the inert oxide such as silica.

SUMMARY OF THE INVENTION

Accordingly, the present invention provides stable, non-agglomerated ultra-small metal/alloy clusters having less than 100 atoms encapsulated in silica wherein the non-agglomerated metal/alloy cluster has size less than 5 nm useful as catalyst.

In an embodiment of the present invention the ultra-small clusters are encapsulated in mono disperse silica particles of 20-30 nm diameter.

In another embodiment of the present invention ultra-small metal/alloy clusters is selected from gold, silver, platinum, palladium either alone or in combination thereof.

In another embodiment of the present invention the ultra-small metal/alloy cluster is stabilized in water medium.

In another embodiment of the present invention ultra-small Au clusters with less than 100 atoms of Au and size less than 5 nm encapsulated in silica.

In another embodiment of the present invention a process for synthesis of stable, non-agglomerated ultra-small clusters of metals/alloy encapsulated in mono-disperse silica particles comprising;
  a) obtaining metal/alloy-thiolate clusters of less than 2 nm by modified Brust method using 3:1 ratio of metal/alloy:thiol in 1:1 mixture of methanol and water, using thiolate ligand N, N, N-Tripropyl (11-mercaptoundecyl) ammonium Chloride and b) encapsulating with silica by one step hydrolysis using tetraethyl orthosilicate (TEOS) in ethanol-water mixture to obtain monodisperse silica spheres encapsulating the metal/alloy-thiolate clusters of less than 2 nm.

In another embodiment of the present invention the nano clusters are encapsulated in mono disperse silica particles of 20-30 nm diameter.

In another embodiment of the present invention further comprising calcining the monodisperse silica particles encapsulating the metal/alloy-thiolate clusters under a flow of air at 350° C., to obtain stable metal clusters with nanoparticle size of ~5 nm.

In another embodiment of the present invention mono-disperse silica particles are a composite.

In another embodiment of the present invention The stable, non-agglomerated ultra-small clusters of metals/alloy encapsulated in mono-disperse silica particles of claim 6, wherein said stable, non-agglomerated ultra-small clusters of metals/alloy encapsulated in mono-disperse silica particles display unique optical properties and show utilization in bio-imaging applications.

DETAILED DESCRIPTION OF INVENTION

The invention will now be described in detail in connection with certain preferred and optional embodiments, so that various aspects thereof may be more fully understood and appreciated and briefly described as follows.

The present invention relates to stable ultra-small metal/alloy clusters, stabilized in water medium, encapsulated in silica where metal/alloy cluster has less than 100 atoms of metal/alloy and cluster size of less than 5 nm.

The composite comprises a hydrophobic ligand, the metal/alloy cluster, SiO2. The ultra-small metal/alloy clusters have less than 100 atoms of the metal/alloy with size of <5 nm and is stable up to 550° C. The novel hydrophobic ligand, in an embodiment, is selected from N,N,N-Tripropyl(11-mercaptoundecyl)ammonium chloride and is prepared by a process known in the art. The novel thiolate ligand enables for cluster stabilization in aqueous medium and also for making the clusters more amenable to silicate precursor assembly and condensation.

In another embodiment, the present invention provides a facile synthesis of water dispersible ultra-small clusters of metals/alloys and their successful encapsulation in mono-disperse silica particles of 20-30 nm diameter.

Encapsulation in porous silica allow diffusion of reactant molecules so that agglomeration and deactivation can be prevented, at the same time keeping the catalytically activity of the clusters intact.

In an embodiment, encapsulation with silica of metals/alloys-thiolate ligand nano-clusters involves a simple one step hydrolysis comprising mixing the metal/alloy-thiolate nano-cluster, with water and ethanol mixture in presence of a base followed by addition of tetraethyl orthosilicate (TEOS) and stirring the mixture at room temperature for two days; wherein the thiolate ligand used is N, N, N-Tripropyl (11-mercaptoundecyl) ammonium Chloride to obtain nano clusters of less than 5 nm.

The metal/alloy-thiolate clusters is obtained by modified Brust method using 3:1 ratio of metal/alloy:thiol in 1:1 mixture of methanol and water, using novel thiolate ligand N, N, N-Tripropyl (11-mercaptoundecyl) ammonium Chloride.

The process for synthesis of stable, non-agglomerated ultra-small clusters of metals/alloy encapsulated in mono-disperse silica particles is as follows:

1. obtaining Au thiolate clusters by modified Brust method using 3:1 ratio of Au:thiol in 1:1 mixture of methanol and water, using thiolate ligand N, N, N-Tripropyl (11-mercaptoundecyl) ammonium Chloride;
2. encapsulating with silica by simple one step hydrolysis using tetraethyl orthosilicate (TEOS) in ethanol-water mixture to obtain monodisperse silica spheres encapsulating the metal clusters;
3. calcining the above monodisperse silica spheres encapsulating the metal clusters under a flow of air at 350° C., to obtain stable metal clusters with nanoparticle size of ~5 nm.

According to Step 1 of the process, to the metal precursor solution dissolved in a polar aprotic solvent is added N, N, N-Tripropyl (11-mercaptoundecyl) ammonium Chloride in methanol and the mixture is stirred for 30 min. Further, NaBH4 solution (1.57 M) in lower alcohol is added and stirring is continued for 45 minutes more. All the steps of reaction are carried out at 0° C. Water is added to gold nanoparticles solution. The solvent is removed by rotavapour. Gold nanocluster in water solution is further purified by dialysis.

The resulting yellow solution of metal or its alloy-thiolate clusters thus obtained by a modified Brust method are characterised by HRTEM and IR, UV-vis and fluorescence spectroscopy.

According to step 2 and 3 of the present invention, the metal/alloy nano cluster solution is mixed with a water-ethanol 1 mixture. Sodium hydroxide solution is added to the mixture followed by addition of tetraethyl orthosilicate (98 wt % Aldrich). The mixture is stirred at room temperature for two days. Silica encapsulated metal/alloy nanocluster is separated from the reaction medium by centrifuging at 14000 rpm and dispersed into ethanol. Silica-encapsulated metal/alloy cluster solution is dried at 100° C. and calcined at 250° C. under air at a ramp rate of 1° $min^{-1}$.

The polar aprotic solvent is selected from acetonitrile, ethyl acetate, acetone, THF etc. The metals are selected from gold, silver, platinum, palladium either alone or a combination thereof.

The process of the invention leads to metal/alloy clusters with optical properties being retained intact after silica coating.

In a preferred embodiment, the present invention relates to stable, non-agglomerated ultra-small gold clusters, stabilized in water medium, encapsulated in silica where the non-agglomerated form of the gold cluster is less than 5 nm and to the process of preparation by a method described herein above.

Figure 1:
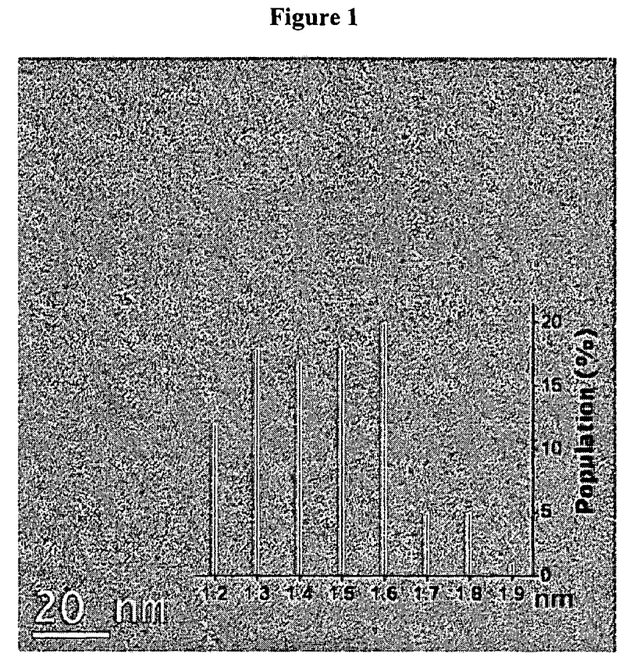
FIG. 1. HRTEM image of the cluster solution

Accordingly, the Au-thiolate clusters is obtained by a modified Brust method by using 3:1 ratio of Au:thiol in a 1:1 mixture of methanol and water. The resulting yellow solution is characterized by HRTEM and IR, UV-vis and fluorescence spectroscopy. HRTEM showed fine particles of a narrow distribution with an average size of 1.2 nm (FIG. 1).

Figure 2:
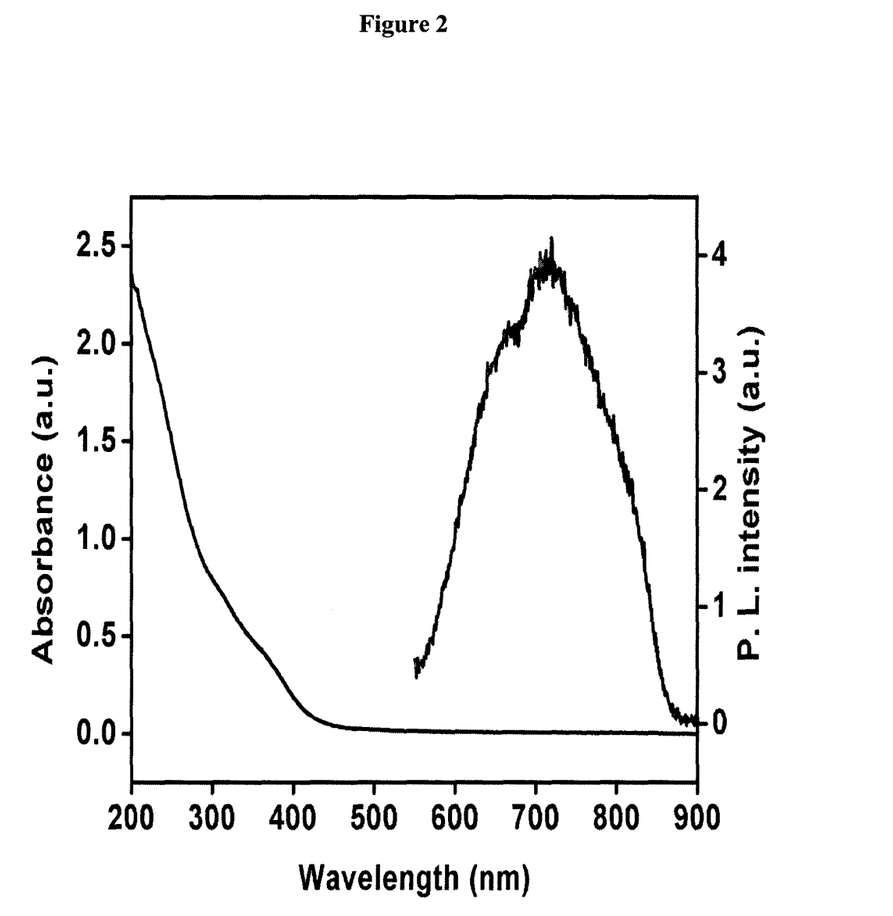
FIG. 2: UV and Fluorescence emission spectra.

This cluster solution is encapsulated with silica using a simple hydrolysis method (modified Stober method) in ethanol-water mixture. HRTEM analysis showed the presence of monodisperse 20-30 nm silica spheres encapsulating the clusters within each. The clusters appear to be intact and separated in space within the silica sphere and not agglomerated (FIG. 2)

Figure 3:
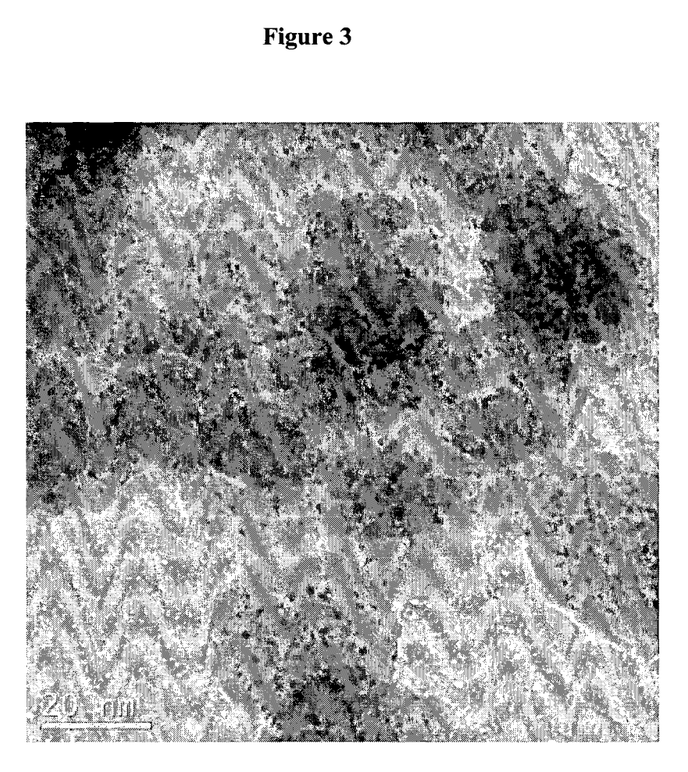
FIG. 3: Au clusters encapsulated inside silica spheres.
Figure 4:
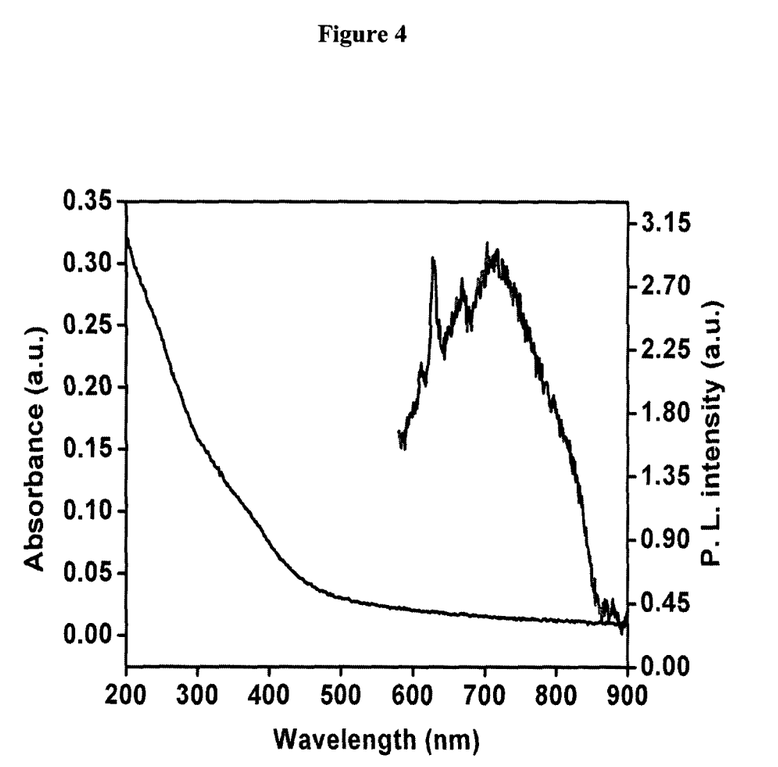
FIG. 4: UV, fluoresence emission spectra after silica coating indicating that the optical properties are intact.

SEM-EDAX analysis showed (FIG. 3) the presence of Au in silica evidencing encapsulation. An EDAX analysis with depth profiling using Focused ion beam milling showed that there is a slight increase in concentration after etching. UV-Vis spectrum of the coated clusters did not show any change from the naked clusters. Fluorescence emission also was found to be intact after silica coating FIG. 4—UV and fluorescence emission spectra after silica coating indicating that the optical properties are intact.

Figure 5:
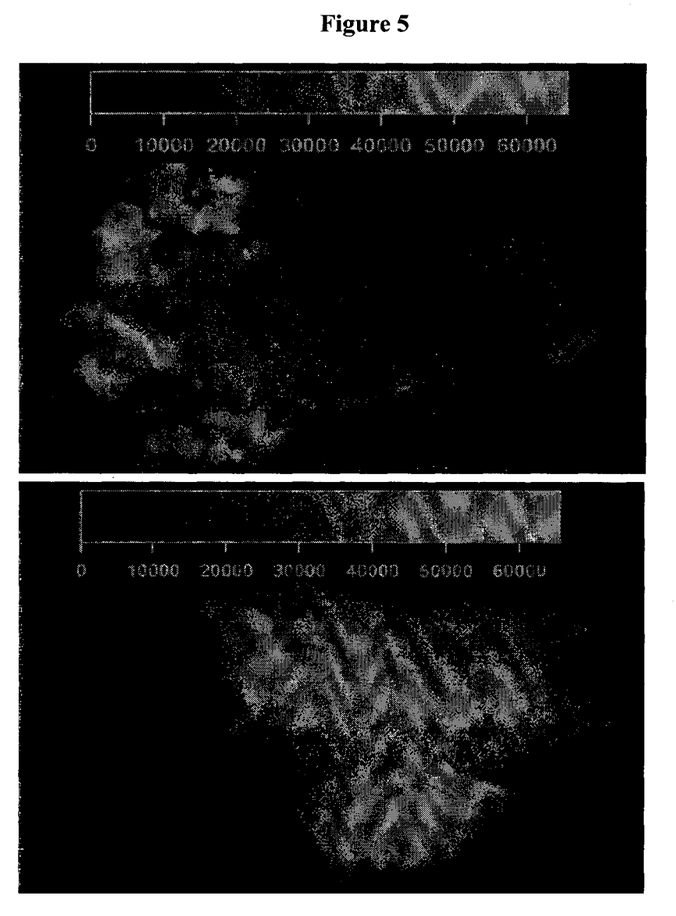
FIG. 5. Fluorescence imaging of pristine as well as silica coated clusters
FIG. 6. TEM of the calcined cluster with porous silica coating
FIG. 7. TEM of Pd@SiO2 after calcinations at (a) 350° C. (b) 500° C. and (c) 750° C.

Fluorescence images (FIG. 5) of both clusters and encapsulated clusters show their utility in bioimaging applications.

Since the number of clusters in one silica sphere is controlled, these Au@SiO2 materials can be used to synthesize size controlled cluster nanoparticles.

Figure 6:
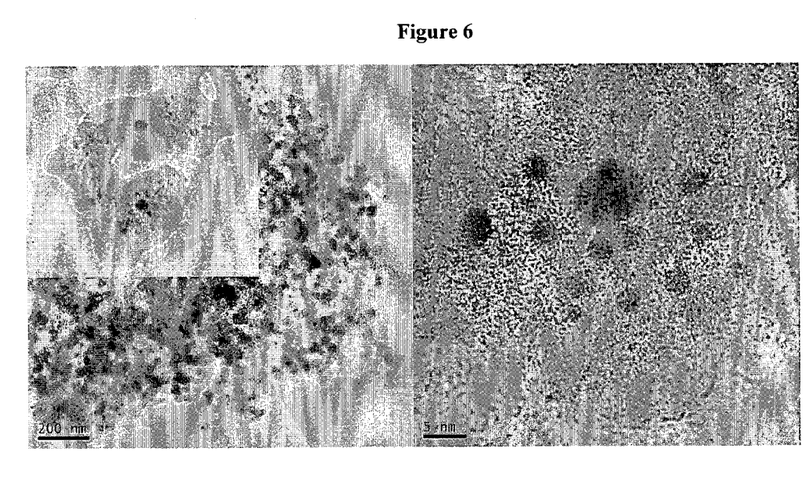
Figure 7:
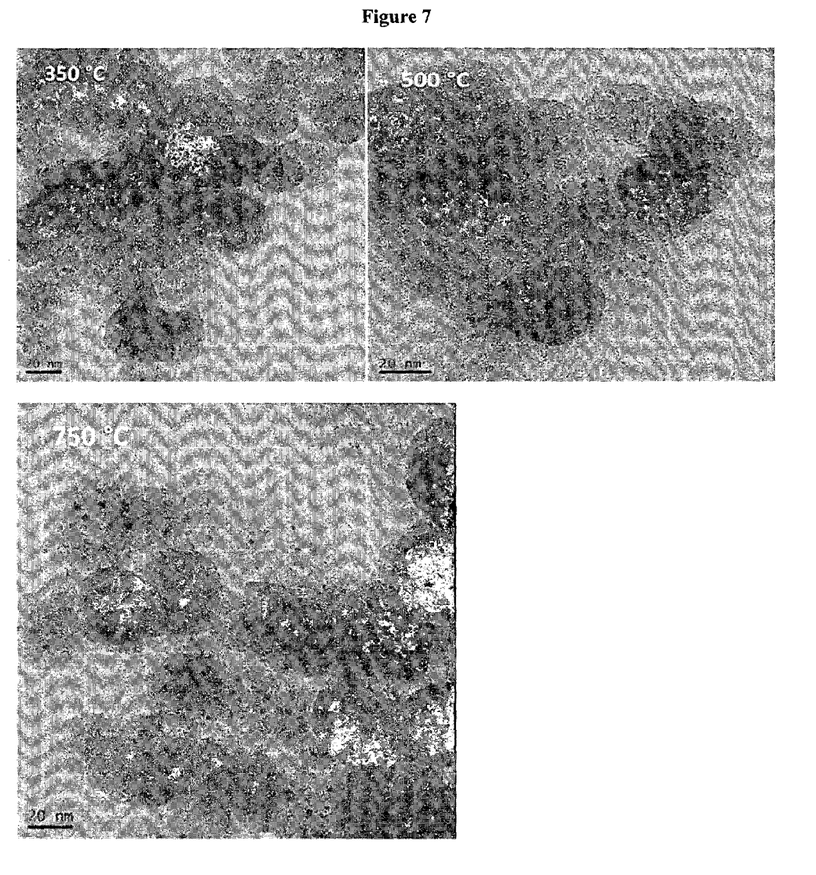

In another embodiment of the invention, controlled calcination under a flow of air at 350° C., the particle size of the metal is almost uniform at ~5 nm. Surprisingly, the silica coating became porous as shown by TEM (FIG. 6).

In yet another embodiment, the present invention relates to Ag, Pd and Pt clusters encapsulated in silica and to the process of preparation thereof.

Further controlled calcinations led to clusters encapsulated in porous silica. Thermal stability of the encapsulated clusters is found to be exceptionally good even at 750° C. in case of Pd.

In another embodiment, a mixture of clusters like Au and Pd are used for encapsulation with silica and later calcination led to the formation of Au—Pd alloy nanoparticles.

The invention provides stable, non-agglomertaed ultra-small metal clusters, stabilized in water medium, encapsulated in silica where the non-agglomerated form of the metal/alloy cluster is less than 5 nm.

In another aspect, the present invention disclose facile synthesis of water dispersible ultra-small clusters of metals and their successful encapsulation in mono-disperse silica particles of 20-30 nm diameter.

Encapsulation in porous silica allow diffusion of reactant molecules so that agglomeration and deactivation can be prevented, at the same time keeping the catalytically activity of the clusters intact.

In an aspect, the invention uses a novel thiolate ligand for cluster stabilization in aqueous medium and for making the clusters more amenable to silicate precursor assembly and condensation using hydrophobic ligand N, N, N-Tripropyl (11-mercaptoundecyl) ammonium Chloride.

In an embodiment, the present invention provides encapsulation with silica of metals/alloys-thiolate ligand nanoclusters involving a simple one step hydrolysis, comprising mixing the metal/alloy-thiolate nano-cluster, with water and ethanol mixture in presence of a base followed by addition of tetraethyl orthosilicate (TEOS) and stirring the mixture at room temperature for two days; wherein the thiolate ligand used is N, N, N-Tripropyl (11-mercaptoundecyl) ammonium Chloride to obtain nano clusters of less than 5 nm.

The metal cluster-composite thus obtained using SiO2 is porous, thermally stable and devoid of agglomeration.

The metal/alloy-thiolate clusters is obtained by modified Brust method using 3:1 ratio of metal/alloy:thiol in 1:1 mixture of methanol and water, using novel thiolate ligand N, N, N-Tripropyl (11-mercaptoundecyl) ammonium Chloride.

The clusters as well as encapsulated systems have unique optical properties and exhibits utilization in bioimaging applications.

The invention is described with reference to preferred embodiments and examples. These examples are indicative of the invention, and should not be construed to narrow down the scope of the invention.

EXAMPLES

Example 1

Synthesis of Thiol Ligand

Synthesis of N,N,N-Tripropyl(11-mercaptoundecyl)ammonium Chloride 11-bromo-1-undecene (5.4 g, 21 mmol) was added to a tripropylamine solution in ethanol (10.2 g, 58 mmol) and stirred for two days under reflux condition at 80° C. The solvent was reduced in vacuo resulting in the bromide salt (S). It was purified by washing (3 times) with hexane (100 ml) under sonication (yield: 93%). 1H NMR ($CDCl_3$, 400 MHz): 5.73-5.83 (m, 1H, CH=$CH_2$), 4.86-4.96 (m, 2H, CH=$CH_2$), 3.31-3.37 (m, 6H, $CH_3CH_2CH_2N^+$), 2.97-3.03 (m, 2H, —$CH_2CH_2N^+$), 1.96-2.03 (q, 7 Hz, 2H, $CH_2$—CH=$CH_2$), 1.62-1.91 (m, 6H, $CH_3H_2CH_2N^+$), 1.19-1.43 (m, 12H, $CH_2$), 1.03 (t, 7 Hz, 9H, $CH_3CH_2CH_2N^+$).

To a solution of (S) (19.0 mmol) in 1:1 mixture of toluene: ethanol Azobisisobutyronitrile (AIBN) (10.0 mmol) and thioacetic acid (80 mmol) were added. The reaction was stirred under reflux for 4 h. The solvents were reduced in vacuo resulting in thioester (G). It was purified by washing (3 times) with a 9:1 mixture of hexane:ethylacetate (100 ml) under sonication.

G was stirred with concentrated hydrochloric acid (2 ml) in methanol (40 ml) under reflux for 12 h. The solvent was then reduced in vacua resulting in thiol F. It was purified by washing (3 times) with a 9:1 mixture of hexane:ethylactate (100 ml) under sonication (yield 75%). 1H NMR ($CDC_3$, 400 MHz): 3.34-3.39 (m, 6H, $CH_2CH_2N^+$), 2.90-3.01 (m, 2H, —$CH_2CH_2N^+$), 2.51-255 (q, 2H, HS—$CH_2$—), 1.58-1.91 (m, 6H, $CH_3CH_2CH_2N^+$), 1.20-1.39 (m, 16H, —$CH_2$), 1.07 (t, 7 Hz, 9H, $CH_3CH_2CH_2N^+$), 0.089-1.03 (m, 2H, —$CH_2CH_2N^+$). IR: 3391, 3141, 2972, 2924, 2857, 2632, 2064, 1624, 1467, 1400, 966, 845, 757, 560 $cm^{-1}$ Example 2

Synthesis of thiol stabilized Gold Nanocluster 8.5 ml $HAuC_4$ solution (10 mmol) in acetonitrile was mixed with 20 ml of acetonitrile. 0.593 g of thiol in 2 ml of methanol was added to this mixture. The mixture was stirred for 30 min. 100 µl $NaBH_4$ solution (1.57 M) in methanol was added and stirring was continued for 45 minutes more. All the steps of reaction were carried out at 0° C. 30 ml water was added with gold nanoparticles solution. Acetonitrile was removed by rotavapour. Gold nanocluster in water. solution was purified by dialysis. UV-visible spectra for gold nanocluster has showed characteristic exponential decay curve. Ratio of thiol to gold (S/Au) was taken 18.

Example 3

Synthesis of Silica Encapsulated Gold Nanocluster

The gold cluster solution was encapsulated with silica using a simple hydrolysis method (modified stober method) in ethanol-water mixture. 500 μGold nanocluster solution was mixed with water (2 ml)-ethanol (8 ml) mixture. 30 μl sodium hydroxide solution (0.1 M) was added to the mixture. 0.05 mmol tetraethyl orthosilicate (98 wt % Aldrich) was added and the mixture was stirred at room temperature two days. Silica encapsulated gold nanocluster was separated from the reaction medium by centrifuging at 14000 rpm and dispersed into ethanol.

Example 4

Synthesis of Porous Silica Encapsulated Au Cluster

Silica-encapsulated gold cluster solution was dried at 100° C. and calcined at 250° C. under air at a ramp rate of 1° $min^{-1}$.

Example 5

Synthesis of Ag cluster 38.5 ml $AgNO_3$ solution (2.2 mM) in water was mixed with 0.148 g of thiol and further 450 μL $NaBH_4$ solution (1.57 M) in methanol was added immediately. Stirring was continued for 60 minutes more. All the steps of reaction were carried out at ice-cooled conditions. Aqueous solution of silver nanocluster was purified by dialysis using cellulose membrane (Aldrich, pore size 12 kDa).

Example 6

Synthesis of Pt Cluster 32.2 ml $H_2PtCl_6$ solution (3.15 mM) in water was mixed with 0.148 g of thiol. The mixture was stirred for 30 min. 450 μl $NaBH_4$ solution (1.57 M) in methanol was added to this mixture and stirring was continued for 60 minutes more. All the steps of reaction were carried out at ice-cooled conditions. Aqueous solution of platinum nanocluster was purified by dialysis using cellulose membrane (Aldrich, pore size 12 kDa).

Example 7

Synthesis of Pd Cluster 32.8 ml $K_2PdCl_4$ solution (2.56 mM) in water was mixed with 0.148 g of thiol. The mixture was stirred for 30 min. 450 μl $NaBH_4$ solution (1.57 M) in methanol was added to this mixture and stirring was continued for 60 minutes more. All the steps of reaction were carried out at ice-cooled conditions. Aqueous solution of palladium nanocluster was purified by dialysis using cellulose membrane (Aldrich, pore size 12 kDa).

Example 8

Synthesis of Silica-Encapsulated Ag Nanocluster

The silver cluster solution was encapsulated with silica using a simple hydrolysis method (modified stober method) in ethanol-water mixture. 500 μl silver nanocluster solution was mixed with water (2 ml)-ethanol (8 ml) mixture. 45 μl sodiumhydroxide solution (0.1 M) was added to the mixture. 0.07 mmol tetraethyl orthosilicate (98 wt % Aldrich) was added and the mixture was stirred at room temperature for two days. Silica encapsulated silver nanocluster was separated from the reaction medium by centrifuging at 14000 rpm and dispersed into ethanol.

Example 9

Synthesis of Silica-Encapsulated Pt Nanocluster

The platinum cluster solution was encapsulated with silica using a simple hydrolysis method (modified stober method) in ethanol-water mixture. 10 ml platinium nanocluster solution was mixed with water (40 ml)-ethanol (160 ml) mixture. 0.9 ml sodiumhydroxide solution (0.1 M) was added to the mixture. 1.35 mmol tetraethyl orthosilicate (98 wt % Aldrich) was added and the mixture was stirred at room temperature for two days. Silica encapsulated platinium nanocluster was separated from the reaction medium by centrifuging at 14000 rpm and dispersed into ethanol.

Example 10

Synthesis of Silica-Encapsulated Pd Nanocluster

The palladium cluster solution was encapsulated with silica using a simple hydrolysis method (modified stober method) in ethanol-water mixture. 10 ml palladium nanocluster solution was mixed with water (40 ml)-ethanol (160 ml) mixture. 0.9 ml sodiumhydroxide solution (0.1 M) was added to the mixture. 1.35 mmol tetraethyl orthosilicate (98 wt % Aldrich) was added and the mixture was stirred at room temperature for two days. Silica encapsulated palladium nanocluster was separated from the reaction medium by centrifuging at 14000 rpm and dispersed into ethanol.

Example 11

Synthesis of Porous Silica Encapsulated Ag Cluster

Silica-encapsulated silver cluster solution was dried at 100° C. and calcined at 350° C. under air at a ramp rate of 1° $min^{-1}$.

Example 12

Synthesis of porous silica encapsulated Pt cluster

Silica-Encapsulated Platinum Cluster Solution was Dried at 100° C. and Calcined at 350° C. Under air at a ramp rate of 1° $min^{-1}$ Example 13

Synthesis of Porous Silica Encapsulated Pd Cluster

Silica-encapsulated palladium cluster solution was dried at 100° C. and calcined at 350° C. under air at a ramp rate of 1° $min^{-1}$.

Example 14

Synthesis Silica Encapsulated Au—Pd Alloy Cluster

Gold and palladium clusters were encapsulated with silica using a simple hydrolysis method (modified stober method)

in ethanol-water mixture. 250 µl gold and 250 µl palladium nanocluster solutions were mixed with water (2 ml)-ethanol (8 ml) mixture. 45 µl sodiumhydroxide solution (0.1 M) was added to the mixture. 0.07 mmol tetraethyl orthosilicate (98 wt % Aldrich) was added and the mixture was stirred at room temperature for two days. Silica encapsulated Au—Pd nanocluster was separated from the reaction medium by centrifuging at 14000 rpm and dispersed into ethanol.

Example 15

Synthesis of Porous Silica Encapsulated Au—Pd Alloy Cluster

Silica-encapsulated Au—Pd cluster solution was dried at 100° C. and calcined at 350° C. under air at a ramp rate of 1° $min^{-1}$.

Example 16

Catalytic Activity of Porous Silica Encapsulated Au Nanoparticle H2O2 and Glucose Detection Using Au Nano-Reactors in Porous Silica To show the peroxidase like activity of the Au nanoreactors, catalytic oxidation of the TMB (3,3',5,5'-Tetramethylbenzidine) was done in presence of $H_2O_2$. In a typical experiment 294 µL of 9.41×10 4 M TMB, 35 µL of stock catalyst solution, 350 µL with different concentrations and 16 µL 160 mM phosphate buffer of pH 7.0 were added and incubated in a 40° C. water bath for 10 minutes. Then the resulting solution was used for absorbance measurement at 650 nm using Perkin-Elmer λ35 spectrophotometer.

In case of glucose detection 20 µL of 2.0 mg/mL Glucose Oxidase and 350 µL glucose with different concentrations and 16 µL 160 mM phosphate buffer 7.0 were incubated at 40° C. water bath for 50 minutes. Then 315 µL of 9.41×10 4 M TMB, 35 µL of stock catalyst solution were added into the above mentioned solution and further the mixed solution was incubated in 40° C. water bath for 10 minutes. Resulting solution was used for absorption spectroscopy measurement.

Figure 8:
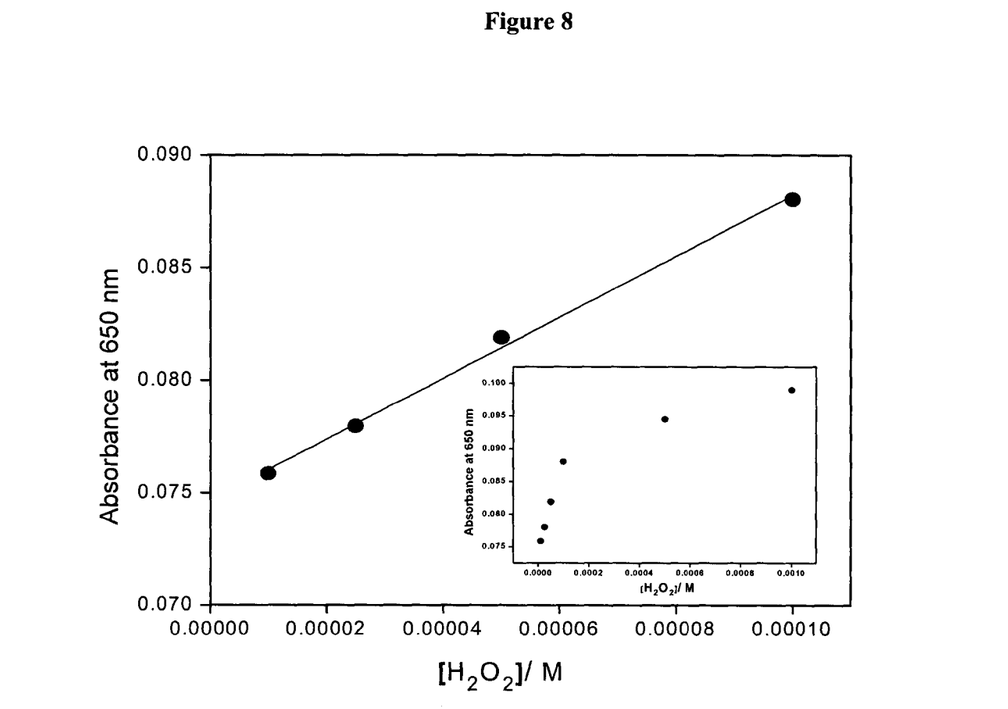
FIG. 8. The Linear calibration plot between the absorbance at 650 nm and concentration of H2O2.

The Linear calibration plot between the absorbance at 650 nm and concentration of H2O2 is shown in FIG. 8. The insert shows the dependence of the absorbance at 650 nm on the concentration of H2O2 in the range 10 µM to 1 mM.

Figure 9:
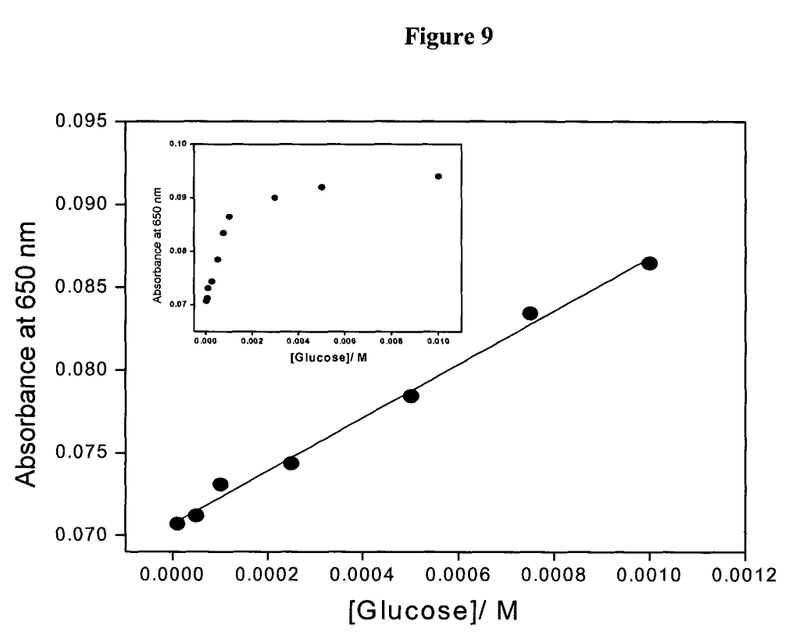
FIG. 9. The Linear calibration plot between the absorbance at 650 nm and concentration of glucose.

The Linear calibration plot between the absorbance at 650 nm and concentration of glucose is shown in FIG. 9. The insert shows the dependence of the absorbance at 650 nm on the concentration of glucose in the range 10 µM to 10 mM.

Example 17

Catalytic Activity of Porous Silica Encapsulated Pd Nanoparticle: Hydrogenation of Trans-Stilbene Trans-Stilbene (180 mg, 1 mmol) and the catalyst (10.3 mg, 0.2 mol % Pd) were mixed in THF (9 ml). The mixture was stirred for 2 h at 25° C. under a H2 balloon. 1,2-diphenylethane was formed with 100% conversion of trans-Stilbene. Product was determined by gas chromatography.

ADVANTAGES OF THE INVENTION

1. Highly thermally stable nano clusters
2. The outer silica shell is porous
3. The porosity enables the clusters to be excellent catalysts
4. Optical properties intact after silica encapsulation
5. The clusters are useful in biological applications

We claim:

1. A process for synthesis of stable, non-agglomerated ultra-small clusters of metals/alloy having size less than 5 nm encapsulated in mono-disperse silica particles comprising;
    a. obtaining metal/alloy-thiolate clusters of less than 2 nm by modified Brust method using a 3:1 ratio of metal/alloy:thiol in a 1:1 mixture of methanol and water, using thiolate ligand N, N, N-Tripropyl (11-mercaptoundecyl) ammonium Chloride;
    b. encapsulating with silica by a one step hydrolysis using tetraethyl orthosilicate (TEOS) in ethanol-water mixture to obtain monodisperse silica spheres encapsulating the metal/alloy clusters having a size less than 2 nm, and
    c. further comprising calcining the monodisperse silica particles encapsulating the ultra-small metal/alloy clusters under a flow of air at 350° C., to obtain stable metal/alloy clusters with a nanoparticle size of less than 5 nm.

2. The process for the encapsulation according to claim 1, wherein the ultra-small clusters of metal/alloy are encapsulated in mono disperse silica particles of 20-30 nm diameter.

\* \* \* \* \*